(12) United States Patent
Sanford

(10) Patent No.: US 7,963,969 B2
(45) Date of Patent: Jun. 21, 2011

(54) PROVISIONAL ORTHOPEDIC IMPLANT AND RECUTTING INSTRUMENT GUIDE

(75) Inventor: Adam H. Sanford, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1216 days.

(21) Appl. No.: 11/643,475

(22) Filed: Dec. 21, 2006

(65) Prior Publication Data

US 2007/0123992 A1    May 31, 2007

Related U.S. Application Data

(62) Division of application No. 10/357,721, filed on Feb. 4, 2003, now Pat. No. 7,172,597.

(51) Int. Cl.
*A61B 17/56* (2006.01)

(52) U.S. Cl. .......................................................... 606/88

(58) Field of Classification Search .............. 606/87–89, 606/96–98, 102, 104; 623/20.14, 20.15, 623/20.21, 20.3, 20.32, 20.35, 23.39
See application file for complete search history.

(56) References Cited

U.S. PATENT DOCUMENTS

| | | | |
|---|---|---|---|
| 4,721,104 A | 1/1988 | Kaufman et al. | |
| 4,787,383 A | 11/1988 | Kenna | |
| 5,053,037 A * | 10/1991 | Lackey | 606/79 |
| 5,122,144 A | 6/1992 | Bert et al. | |
| 5,258,032 A | 11/1993 | Bertin | |
| 5,314,482 A | 5/1994 | Goodfellow et al. | |
| 5,445,642 A | 8/1995 | McNulty et al. | |
| 5,458,645 A | 10/1995 | Bertin | |
| 5,520,695 A | 5/1996 | Luckman | |
| 5,683,397 A | 11/1997 | Vendrely et al. | |
| 5,702,460 A | 12/1997 | Carls et al. | |
| 5,733,292 A | 3/1998 | Gustilo et al. | |
| 5,776,201 A | 7/1998 | Colleran et al. | |
| 5,879,393 A | 3/1999 | Whiteside et al. | |
| 5,885,296 A | 3/1999 | Masini | |
| 5,989,261 A | 11/1999 | Walker et al. | |
| 6,080,196 A | 6/2000 | Bertin | |
| 6,096,043 A | 8/2000 | Techiera et al. | |

OTHER PUBLICATIONS

Informational Pamphlet—Zimmer 1999, Revision Knee Arthroplasty Surgical Guidelines, pp. 1-39.
Brochure—Zimmer 2002, MIS Minimally Invasive Solution, Intramedullary Surgical Approach, The M/G Unicompartmental Knee Minimally Invasive Surgical Technique, pp. 1-24.
Brochure—Zimmer 1998, 2000—NexGen Complete Knee Solution, Multi-Reference 4-in-1 Femoral Instrumentation Posterior Reference Surgical Technique, pp. 1-16.

(Continued)

*Primary Examiner* — Eduardo C Robert
*Assistant Examiner* — David Comstock
(74) *Attorney, Agent, or Firm* — Baker & Daniels LLP

(57) ABSTRACT

A provisional component for use with differently sized first and second prosthetic orthopedic components. The provisional component has a configuration which is substantially similar to the first prosthetic component and has a predefined correspondence to the second prosthetic component. The provisional component is mounted on a bone to assess the fit of the first prosthetic component. The provisional component includes a referencing element for defining a reference point on the bone if the fit of the provisional component indicates that the second prosthetic component should be used. An instrument guide is aligned with the reference point and used to properly position a surgical instrument to prepare the bone to receive the second prosthetic component. The provisional and prosthetic components may all be femoral components which have an articulating surface defining a single condylar-shaped projection.

5 Claims, 3 Drawing Sheets

OTHER PUBLICATIONS

Brochure—Zimmer 1995, 1997, 1998—NexGen Complete Knee Solution, Intramedullary Instrumentation Surgical Technique, pp. 1-33.

Brochure—Zimmer 2001—NexGen Complete Knee Solution, Revision Instrumentation Surgical Technique for Legacy Knee Constrained Condylar Knee, pp. 1-78.

* cited by examiner

PROVISIONAL ORTHOPEDIC IMPLANT AND RECUTTING INSTRUMENT GUIDE

CROSS REFERENCE TO RELATED APPLICATIONS

This is a Divisional of U.S. patent application Ser. No. 10/357,721, filed Feb. 4, 2003, now U.S. Pat. No. 7,172,597, the disclosure of which is hereby expressly incorporated herein by reference.

BACKGROUND

1. Field of the Invention

The present invention relates to orthopedic prostheses and, more particularly, to a provisional orthopedic prosthetic component that can be used to facilitate the selection of one of at least two differently configured permanent prosthetic components and the proper positioning of an instrument guide for preparing the bone that will receive the permanent prosthetic component.

2. Description of the Related Art

The use of orthopedic implants to form artificial joints such as prosthetic knees is well known in the art. During a conventional surgical procedure to implant a prosthetic knee joint, a provisional femoral component and a provisional tibial component are placed on the distal femur and proximal tibia after resecting the distal femur and proximal tibia to confirm the proper size and position of the permanent femoral and tibial components. The provisional components typically come in a range of sizes which are identical in size and shape to the permanent components. The provisional components which are placed on the resected femur and tibia are typically selected after making a preliminary determination of the proper size. A trial reduction of the knee joint with the provisional components in place may indicate that the preliminary size determination was incorrect, that the gap between the femur and tibia is insufficient, or some other undesirable characteristic which requires the selection of a different sized tibial or femoral component thereby necessitating the further resection of either the tibia or femur.

When it is determined that the preliminary size determination of the femoral component is incorrect and the femur must be recut, the provisional component is removed. An instrument guide must then be properly located on the femur to recut the femur to receive the newly selected femoral component. After conducting another trial reduction to confirm the selection of the new prosthetic components, the newly selected prosthetic components are implanted.

Although this method of implanting an orthopedic prosthesis is satisfactory, an improved method reducing the number of required steps when the preliminarily selected prosthetic component size is changed would be desirable.

SUMMARY

The present invention provides a provisional component for an orthopedic prosthesis which includes a referencing element which may be used to define a reference point on the bone if the size of the preliminary prosthetic component must be changed. The reference point may then be used to align an instrument guide to recut or otherwise prepare the bone for receiving the newly selected prosthetic component.

The invention comprises, in one form thereof, a system for implanting an orthopedic prosthesis on a bone using a surgical tool. The system includes a first prosthetic component and a second prosthetic component wherein the first and second prosthetic components have differently sized configurations. A provisional component removably mountable on the bone is also provided. The provisional component has a configuration that is substantially similar to the first prosthetic component and has a predefined correspondence to the second prosthetic component. At least one referencing element is disposed on the provisional component wherein, when the provisional component is mounted on the bone, the at least one referencing element defines at least one reference point on the bone. The system also includes an instrument guide having at least one positioning element alignable with the at least one reference point. The instrument guide defines at least one guide feature engageable with the surgical tool wherein alignment of the positioning element with the reference point positions the guide feature to engageably align the surgical tool to prepare the bone to receive the second prosthetic component.

The at least one referencing element may be a plurality of passages extending through the provisional component. The system may also include at least one headless pin wherein the pin is registrable with the referencing element to position the pin for mounting in the bone at the reference point. The pin is also engageable with the positioning element whereby the positioning element is aligned with the reference point.

The at least one guide feature in the instrument guide may define a slot engageable with a cutting instrument or an opening engageable with a drilling instrument. The second prosthetic component may also be smaller than the first prosthetic component.

In some embodiments, the provisional component, the first prosthetic component and the second prosthetic component each include an inwardly facing surface configuration having at least three intersecting planar surfaces wherein the inward facing surface configuration of the provisional component and the first prosthetic component is larger than the inward facing surface configuration of the second prosthetic component. The instrument guide has a base surface engageable with a substantially planar surface on the bone and the at least one guide feature includes first and second slots intersecting the base surface and engageable with a cutting instrument. The first slot is positioned non-parallel to the second slot wherein the base surface, the first slot and the second slot define three intersecting planes having a configuration substantially similar to the inward facing surface of the second prosthetic component.

The invention comprises, in another form thereof, a system for implanting an orthopedic prosthesis on a bone using a surgical tool. The system includes a first prosthetic component and a second prosthetic component wherein the first and second prosthetic components have differently sized configurations. A provisional component removably mountable on the bone is also provided. The provisional component has a configuration that is substantially similar to the first prosthetic component and has a predefined correspondence to the second prosthetic component. At least one registry surface is disposed on the provisional component. At least one alignment member is engageable with the at least one registry surface wherein, when the provisional component is mounted on the bone, engagement of the alignment member with the registry surface positions the alignment member for mounting on the bone. The system also includes an instrument guide having at least one positioning element engageable with the at least one alignment member. The instrument guide defines at least one guide feature engageable with the surgical tool wherein engagement of the positioning element with the alignment member positions the guide feature to engageably align the surgical tool for preparing the bone to receive the second prosthetic component.

The at least one registry surface may be the interior surface of a passage extending through the provisional component and the alignment member may be a headless pin. The provisional component, first prosthetic component and second prosthetic component may each be adapted for mounting on a distal femur and each include an outwardly facing surface defining a single condylar-shaped projection.

The invention comprises, in yet another form thereof, a method of implanting an orthopedic prosthesis. The method includes providing a first prosthetic component and a second prosthetic component wherein the first and second prosthetic components have differently sized configurations. Also provided is a provisional component having a configuration that is substantially similar to the first prosthetic component and has a predefined correspondence to the second prosthetic component and wherein at least one referencing element is disposed on the provisional component. The method also includes preparing a bone to receive the first prosthetic component, mounting the provisional component to the bone, and assessing the fit of the provisional component and selecting one of the first and second prosthetic components for implantation based upon the assessment of the fit of the provisional component. When the first prosthetic component is selected for implantation, the method includes implanting the first prosthetic component on the bone without further substantial modification of the bone following removal of the provisional component. When the second prosthetic component is selected for implantation, the method includes (a) marking at least one reference point on the bone at a location defined by the reference element; (b) aligning an instrument guide with the reference point on the bone; (c) positioning a surgical instrument using the instrument guide and preparing the bone with the surgical instrument for receiving the second prosthetic component; and (d) implanting the second prosthetic component.

The at least one referencing element may be a registry surface disposed on the provisional component and the step of marking at least one reference point on the bone may include registering at least one alignment member with the at least one registry surface and mounting the alignment member in the bone in the position determined by registration of the alignment member and the registry surface. The instrument guide may also include at least one positioning element and the step aligning the instrument guide with the reference point includes registering the at least one positioning element with the at least one alignment member after mounting the alignment member in the bone.

The at least one referencing element may be a passage extending through the provisional component and the step of marking at least one reference point on the bone may include positioning at least one headless pin in the at least one passage and mounting the pin in the bone at the location defined by the referencing element. The instrument guide may also include at least one positioning element and the step of aligning the instrument guide with the reference point includes registering the at least one pin with the at least one positioning element after mounting the pin in the bone.

The step of preparing a bone to receive the first prosthetic component may include preparing a distal femur to receive the first prosthetic component and the provisional component, first prosthetic component and second prosthetic component may each include an outwardly facing surface that defines a single condylar-shaped projection.

The provisional component, first prosthetic component and second prosthetic component may each include an inwardly facing surface configuration having at least three intersecting planar surfaces wherein the inward facing surface configuration of the provisional component and the first prosthetic component is larger than the inward facing surface configuration of the second prosthetic component. The step of preparing a bone to receive the first prosthetic component includes forming at least three intersecting planar surfaces on the bone corresponding to the inward facing surface configuration of the provisional component and the first prosthetic component and the step of positioning a surgical instrument using the instrument guide and preparing the bone with the surgical instrument for receiving the second prosthetic component includes recutting at least one of the three intersecting planar surfaces on the bone.

An advantage of the present invention is that it provides a provisional component that may be used to assess the fit of a orthopedic prosthetic component and, if the assessment indicates that a differently sized prosthetic component should be selected, the provisional component includes referencing elements which may be used to mark the bone to properly align an instrument guide on the bone to recut or otherwise prepare the bone to receive the newly selected prosthetic component. This provides a relatively convenient procedure for revising the bone surface to receive the newly selected prosthetic component which simplifies the alignment of the instrument guide on the bone.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
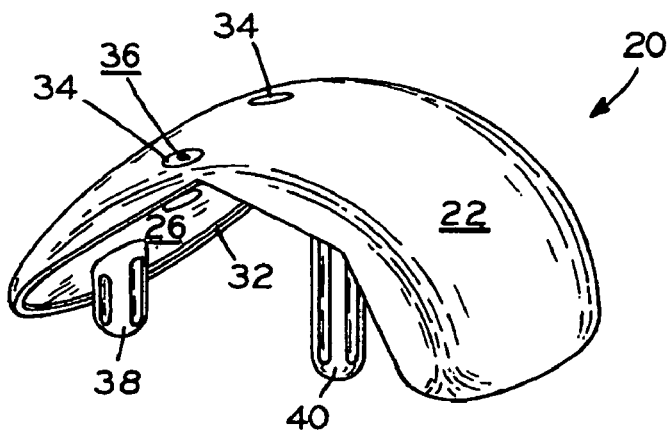
FIG. 1 is a perspective view of a provisional component in accordance with the present invention.
Figure 2:
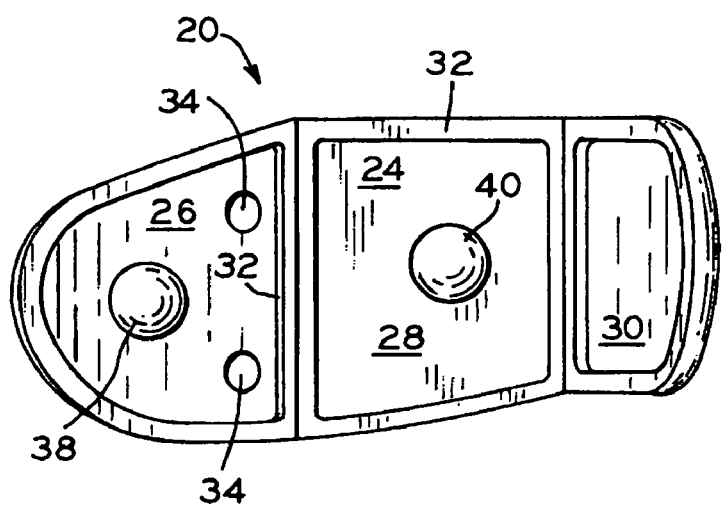
FIG. 2 is a top view of the provisional component of FIG. 1.
Figure 3:
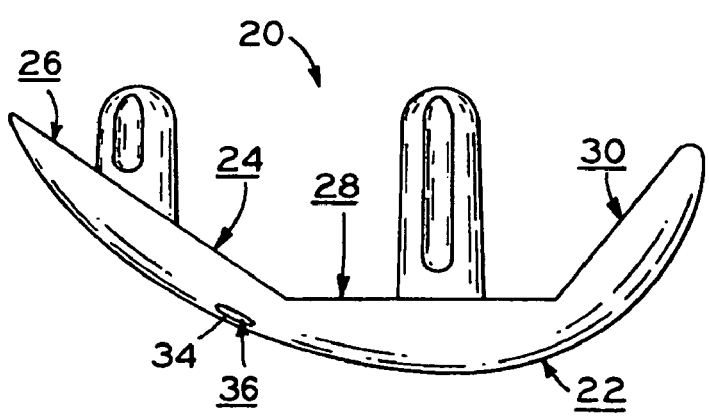
FIG. 3 is a side view of the provisional component of FIG. 1.
Figure 4:
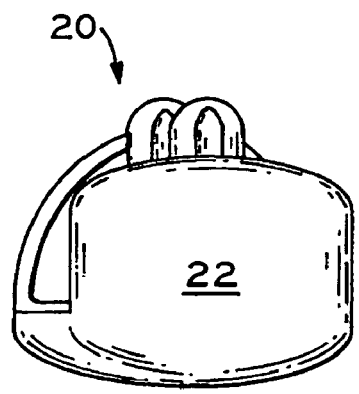
FIG. 4 is a posterior view of the provisional component of FIG. 1.

Corresponding reference characters indicate corresponding parts throughout the several views. Although the exemplification set out herein illustrates an embodiment of the invention, the embodiment disclosed below is not intended to be exhaustive or to be construed as limiting the scope of the invention to the precise form disclosed.

DETAILED DESCRIPTION

A provisional component 20 in accordance with the present invention is shown in FIG. 1. Provisional component 20 has an outwardly facing surface 22 which defines a single condylar-shaped projection and an oppositely disposed inward facing surface 24. Inward facing surface 24 has three substantially planar sections 26, 28, 30. A small ridge 32 defines the perimeter of the three intersecting planar sections 26, 28 and 30. Cylindrical openings extending from outer surface 22 to inner surface 24 define passages 34. The interior surface of passages 34 defines a registry surface 36 as discussed in greater detail below. Mounting posts 38, 40 are provided for removably mounting provisional component 20 to a femur 42.

Figure 5:
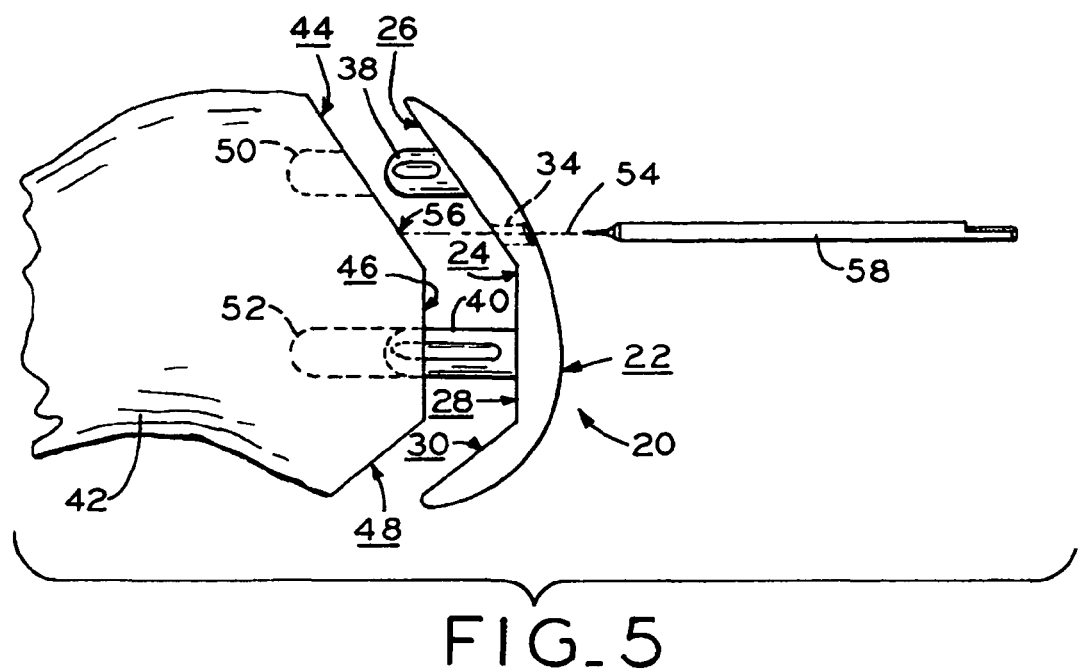
FIG. 5 is a view of an exploded view of the provisional component, a pin and a femur.

The mounting of provisional component 20 to a femur 42 is best seen in FIG. 5. In FIG. 5, femur 42 has been resected leaving a distal cut 44, a chamfer cut 46 and a posterior cut 48. Resected surfaces 44, 46, 48 define three intersecting planes having a configuration that is substantially similar to the configuration of the inwardly facing planar surfaces 26, 28, 30 of provisional component 20, i.e., the angles between surfaces 44, 46, 48 are the same as the angles between surfaces 26, 28, 30 and the length of surface 46 between surfaces 44 and 48 is the same as the length of surface 28 between surfaces 26, 30 whereby surfaces 26, 28, 30 may engage surfaces 44, 46, 48 respectively in a substantially flush manner. Bores 50, 52 are also located on femur 42 and receive mounting posts 38, 40 of provisional component 20 to thereby mount provisional component 20 on femur 42. After inserting mounting posts 38, 40 into bores 50, 52, provisional component 20 is pushed onto femur 42 until inner surfaces 26, 28, 30 engage bone surfaces 44, 46, 48. Femur 42 is prepared to receive a femoral component having the configuration of provisional component 20 in a conventional manner. Alternative methods of preparing femur 42 to receive provisional component 20 are described by Sanford et al. in U.S. Pat. No. 6,916,324, entitled PROVISIONAL ORTHOPEDIC PROSTHESIS FOR PARTIALLY RESECTED BONE, filed on Feb. 4, 2003, and issued on Jul. 12, 2005, and in U.S. patent application Ser. No. 10/358,010, entitled PROVISIONAL ORTHOPEDIC IMPLANT WITH REMOVABLE GUIDE, filed on Feb. 4, 2003, both of which are hereby expressly incorporated herein by reference.

Passage 34 functions as a referencing element and after provisional component 20 has been mounted to femur 42 axis 54 of passage 34 defines a reference point 56 on femur 42. As can also be seen in FIG. 5, engaging or registering an alignment member such as headless holding pin 58 with registry surface 36 which defines passage 34 positions pin 58 so that it may be mounted in femur 42 at reference point 56. Alternative embodiments may employ other referencing elements and registry surfaces for defining a reference point on the bone or positioning an alignment member. A hole for receiving pin 58 may be pre-drilled prior to inserting pin 58 by using passage 34 as a drill guide. The use of pin 58 to mount instrument guide 60 on femur 42 is discussed in greater detail below.

Figure 6:
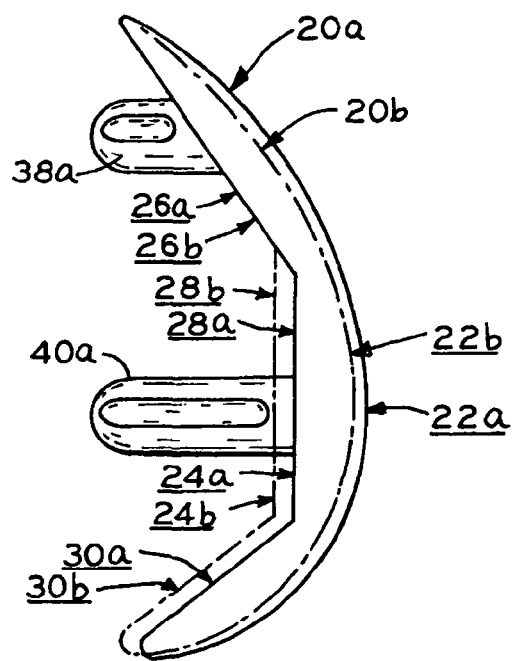
FIG. 6 is a view showing the relative sizes of two prosthetic components.

First and second permanent orthopedic prosthetic components 20a and 20b are shown in FIG. 6 with second prosthetic component 20b being shown in dashed outline. First and second prosthetic components 20a and 20b have a common design and outer surfaces 22a, 22b each define a single condylar shaped projection wherein each prosthetic component 20a, 20b is configured to replace either a right lateral or left medial condylar surface. First prosthetic component 20a, however, is larger than second prosthetic component 20b and first and second prosthetic components 20a, 20b thus form two different sizes of a femoral prosthetic component design.

During the preliminary evaluation of a patient, a surgeon will make a preliminary selection of the size of the prosthetic component to be implanted. In the illustrated embodiment, first prosthetic component 20a is the preliminarily selected component and second prosthetic component 20b is the immediately smaller size component. Consequently, provisional component 20 has a configuration that is substantially similar to first prosthetic component 20a. Provisional component 20 also a predefined correspondence to second prosthetic component 20b, i.e., provisional component 20 and second prosthetic component 20b have a common overall design but do not have the same size. The placement of passages 34 on provisional component 20 is also related to second prosthetic component 20b as discussed in greater detail below.

The sole difference between first prosthetic component 20a and provisional component 20 is that provisional component 20 includes reference elements 34. As can be seen in FIG. 6, second prosthetic component 20b has a configuration which shares a common design but which is smaller than the common configuration of first prosthetic component 20a and provisional component 20. In the illustrated embodiment, the mounting posts of second prosthetic component 20b are disposed in the same relative locations as the mounting posts of first prosthetic component 20a. Alternative embodiments of the present invention may employ prosthetic components wherein the relative position of the mounting posts are not common to each of the differently sized prosthetic components.

In FIG. 6, those features of first provisional component 20a which are found on provisional component 20 are identified with the same reference numeral used with provisional component 20 and include the suffix "a". Similarly, such common features identified on second provisional component 20b are identified using the same reference numeral used with provisional component 20 and include the suffix "b". A description of these common features is not repeated.

The common configuration of inward facing surface 24, 24a of provisional component 20 and first prosthetic component 20a is larger than the configuration of inward facing surface 24b of second prosthetic component 20b whereby a femur 42 which has been prepared to receive first prosthetic component 20a can have additional bone material removed to reshape the distal end of femur 42 to receive the smaller sized second prosthetic component 20b.

At the same time that femur 42 is prepared to receive the preliminarily selected prosthetic component 20a, tibia 80 is also prepared to receive an implant by resecting the right lateral tibial plateau to leave resected surface 82. Provisional component 20 is then mounted on femur 42 as discussed above and a provisional tibial component (not shown) having the same configuration as the preliminarily selected permanent tibial component is mounted on tibial surface 82. After mounting the provisional prosthesis formed by the provisional femoral and tibial components, a trial reduction is performed by the surgeon to assess the fit of thereof. The trial reduction involves re-engaging tibia 80 and femur 42 whereby the femoral provisional component 20 is engaged with the provisional tibial component and relatively moving tibia 80 and femur 42 between flexion and extension positions and examining the fit of the provisional components throughout this range of motion. After conducting the trial reduction of provisional component 20, the surgeon may decide that the preliminarily selected component size and position was correct. If this is the case, the surgeon will then remove provisional component 20 and implant first prosthetic component 20a in a conventional manner.

The trial reduction may also lead the surgeon to conclude that the preliminarily selected component size was incorrect. For example, the trial reduction may show that the preliminarily selected prosthesis size places the soft tissues surrounding the joint in excessive tension and a smaller prosthesis size should be implanted. If the surgeon decides that the next smaller size femoral component, e.g., second prosthetic component 20*b*, is the appropriate size to implant on femur 42, the surgeon will position holding pins 58 in passages 34 and mount pins 58 at reference points 56 on femur 42. Provisional component 20 will then be removed from femur 42 leaving pins 58 mounted thereon. As can be seen in FIG. 5, axes 54 of passages 34 are positioned parallel to mounting posts 38, 40 so that provisional component 20 may be retracted without disturbing the position of pins 58.

Figure 7:
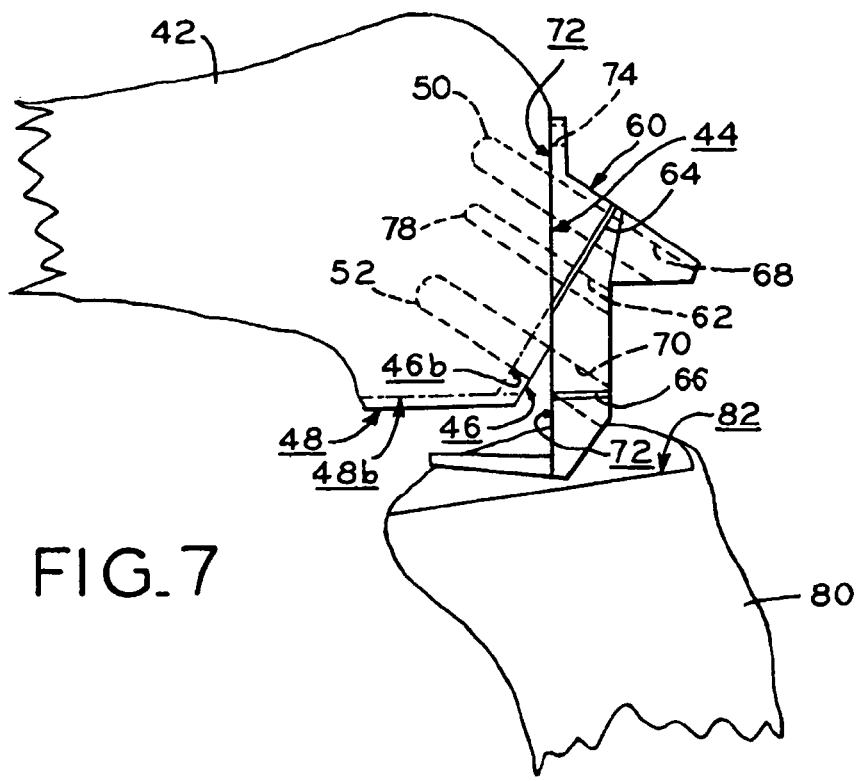
FIG. 7 is a side view of femur and tibia with an instrument guide mounted on the femur.
Figure 8:
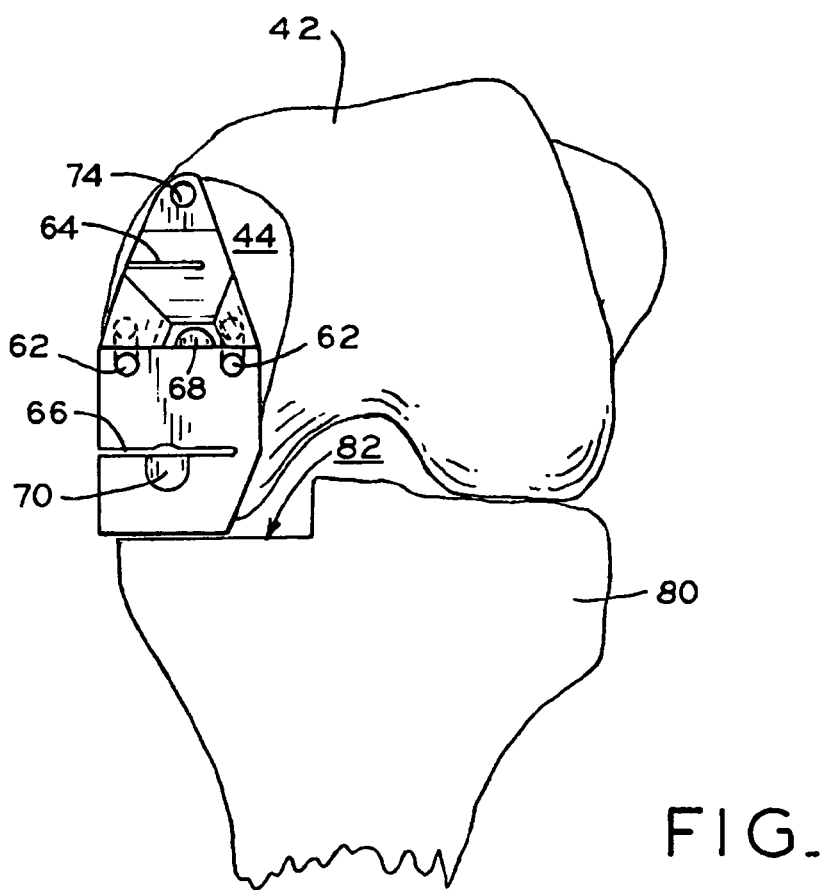
FIG. 8 is a front view of a femur and a tibia with an instrument guide mounted on the femur.

After removing provisional component 20 from pins 58, instrument guide 60 is mounted on femur 42. Instrument guide 60 is illustrated in FIGS. 7 and 8 and includes two positioning elements which take the form of openings 62 which are alignable with reference points 56 to position instrument guide 60 on femur 42 in a desired location. Mounting instrument guide 60 on femur 42 involves sliding pins 58 into openings 62. Dashed outline 78 shown in FIG. 7, indicates the position of that portion of pins 58 located within femur 42. An aperture 74 is located near the anterior end of instrument guide 60 and a bone screw (not shown) or other suitable fastener is inserted therethrough to firmly secure instrument guide 60 to femur 42 after positioning instrument guide 60 on femur 42 after sliding pins 58 into openings 62. Alternative embodiments may include apertures or other mounting features positioned at other locations on instrument guide 60.

Instrument guide 60 also includes guide features for engaging a surgical tool to thereby position the tool for preparing femur 42 to receive second prosthetic component 20*b*. In the illustrated embodiment, the guide features include cutting slots 64, 66 and drill guide openings 68, 70. The position of passages 34 on provisional component 20 are coordinated with positioning elements 62 on instrument guide 60 so that when instrument guide 60 is aligned with the reference points defined on femur 42 by referencing elements 34, instrument guide 60 will be properly positioned on femur 42 so that guide features 64, 66, 68, 70 may be used to properly position surgical tools to prepare femur 42 to receive second prosthetic component 20*b*.

More specifically, engagement of a cutting instrument with cut slot 64 will position the cutting instrument for making chamfer cut 46*b* (shown as a dashed line in FIG. 7). Similarly, engagement of a cutting instrument with cut slot 66 will position the cutting instrument for making posterior cut 48*b*. As can be seen in FIG. 7, a small portion of femur 42 will be removed to form chamfer cut 46*b* and posterior cut 48*b*.

Engagement of a drilling instrument with drill guide 68 positions the instrument to form bore 50. Similarly, inserting a drill bit into drill guide 70 properly positions the drill bit to form bore 52. In the illustrated embodiment, the relative positions of mounting posts 38*a*, 40*a* and mounting posts 38*b*, 40*b* are similar and the bores prepared to receive mounting posts 38*a*, 40*a* of first prosthetic component 20*a* are suitable for receiving mounting posts 38*b*, 40*b* of second prosthetic component 20*b* although it may be desirable to increase the depth of bore 52. If, however, bores 50, 52 did not align with mounting posts 38*b*, 40*b*, drill guides 68, 70 could be used to properly position a drill or other suitable instrument to recut new bores in femur 42 to receive mounting posts 38*b*, 40*b*.

Although the illustrated embodiment employs a second prosthetic component which is smaller than first prosthetic component 20*a* and configured whereby femur 42 may be prepared to flushly engage the entire inner surface 24*b* of second prosthetic component 20*b* alternative embodiments might require bone cement or other suitable material to be used to fill in certain areas of the bone receiving the newly selected prosthetic component to properly receive the newly selected component. For example, the newly selected component in alternative embodiments might differ in design or have features which are not smaller than the originally selected prosthetic component. Alternative embodiments of the present invention may also include provisional components having more than one set of referencing elements or registration surfaces whereby the provisional component may be used to position an instrument guide for more than one differently sized component. For example, by including another set of passages in provisional component 20 and another suitable instrument guide, the surgeon could elect to position pins 58 in femur 42 in this second set of passages and select a femoral component which was two sizes smaller than the originally selected prosthetic component 20*a*.

Instrument guide 60 includes a substantially planar base surface 72 that is positioned flush with distal bone surface 44 when instrument guide 60 is mounted on femur 42. Cutting slots 64, 66 intersect base surface 72 at non-parallel angles whereby slots 64, 66 together with base surface 72 define three intersecting planar sections which have a configuration substantially similar to inward facing surface 24*b* of second prosthetic component 20*b*. More specifically, the plane defined by base surface 72 corresponds to surface 26*b*, cutting plane 46*b* defined by cut slot 64 corresponds to surface 28*b* and cutting plane 48*b* defined by cut slot 66 corresponds to surface 30*b*. Due to the presence of holding pins or bone screws securing instrument guide 60 to femur 42, chamfer cut 46*b* and posterior cut 48*b* may require that instrument guide 60 and all securing fasteners be removed from femur 42 prior to finishing the cuts and removing all extraneous bone from femur 42.

After removing instrument guide 60 and cleaning off any extraneous bone from femur 42, a provisional component having the same size as second prosthetic component 20*b* is removably mounted on femur 42 to assess the fit of second prosthetic component 20*b*. A provisional tibial component is also employed. The change of the femoral component may require that a differently sized tibial component be used, possibly requiring that tibia 80 be recut to form a new resection surface 82. If the provisional prosthesis confirms the selection of second prosthetic component 20*b*, component 20*b* is then implanted.

Although the disclosed embodiment is used in the implantation of a partial knee prosthesis, the present invention could also be employed with a total knee prosthesis or with orthopedic prosthetic components adapted for use at other anatomical locations.

While this invention has been described as having an exemplary design, the present invention may be further modified within the spirit and scope of this disclosure. This application is therefore intended to cover any variations, uses, or adaptations of the invention using its general principles.

What is claimed is:

1. A method of implanting an orthopedic prosthesis, said method including:
providing a first prosthetic component and a second prosthetic component, said first and second prosthetic components having differently sized configurations and a provisional component having a configuration that is substantially similar to said first prosthetic component and has a predefined correspondence to said second prosthetic component and wherein at least one referencing element is disposed on said provisional component;
preparing a bone to receive said first prosthetic component;

after preparing step, mounting said provisional component to the bone;

after said mounting step, assessing the fit of said provisional component and selecting one of said first and second prosthetic components for implantation based upon the assessment of the fit of said provisional component;

wherein when said first prosthetic component is selected for implantation, said method includes implanting said first prosthetic component on the bone without further substantial modification of the bone after said preparing step and following step of removing the provisional component; and wherein when said second prosthetic component is selected for implantation, said method includes, after said step of selecting one of said first and second prosthetic components for implanting the following steps (a), (b), (c) and (d): (a) marking at least one reference point on the bone at a location defined by said reference element; (b) aligning an instrument guide with the reference point on the bone; (c) positioning a surgical instrument using said instrument guide and preparing the bone with the surgical instrument for receiving said second prosthetic component; and (d) implanting the second prosthetic component.

2. The method of claim 1 wherein said at least one referencing element comprises at least one registry surface disposed on said provisional component and said step of marking at least one reference point on the bone includes registering at least one alignment member with said at least one registry surface and mounting said alignment member in the bone in the position determined by registration of said alignment member and said registry surface and wherein said instrument guide includes at least one positioning element and said step aligning said instrument guide with the reference point includes registering said at least one positioning element with said at least one alignment member after mounting said alignment member in the bone.

3. The method of claim 1 wherein said at least one referencing element comprises at least one passage extending through said provisional component and said step of marking at least one reference point on the bone comprises positioning at least one headless pin in said at least one passage and mounting said pin in the bone at the location defined by said referencing element and wherein said instrument guide includes at least one positioning element and said step of aligning said instrument guide with the reference point includes registering said at least one pin with said at least one positioning element after mounting said pin in the bone.

4. The method of claim 1 wherein said step of preparing a bone to receive said first prosthetic component comprises preparing a distal femur to receive said first prosthetic component and wherein said provisional component, said first prosthetic component and said second prosthetic component each include an outwardly facing surface defining a single condylar-shaped projection.

5. The method of claim 1 wherein said provisional component, said first prosthetic component and said second prosthetic component each include an inwardly facing surface configuration having at least three intersecting planar surfaces, said inward facing surface configuration of said provisional component and said first prosthetic component being larger than said inward facing surface configuration of said second prosthetic component;

wherein said step of preparing a bone to receive said first prosthetic component includes forming at least three intersecting planar surfaces on the bone corresponding to said inward facing surface configuration of said provisional component and said first prosthetic component; and wherein said step of positioning a surgical instrument using said instrument guide and preparing the bone with the surgical instrument for receiving said second prosthetic component includes recutting at least one of the three intersecting planar surfaces on the bone.

\* \* \* \* \*